US00PP23585P3

(12) United States Plant Patent
Clark et al.

(10) Patent No.: US PP23,585 P3
(45) Date of Patent: May 7, 2013

(54) COLEUS PLANT NAMED 'UF0843'

(50) Latin Name: *Solenostemon scutellariodes*
Varietal Denomination: UF0843

(75) Inventors: David G. Clark, Gainesville, FL (US); Grayson Clark, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 76 days.

(21) Appl. No.: 13/317,096

(22) Filed: Oct. 8, 2011

(65) Prior Publication Data

US 2012/0260376 P1 Oct. 11, 2012

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner* — Annette Para

(57) ABSTRACT

'UF0843' is a novel coleus plant distinguished by having excellent bold lemon-lime/green-yellow foliage color which maintains bright color in both sun and shade conditions, novel leaf shape, excellent vigor, and desirable late-flowering characteristics, as disclosed.

2 Drawing Sheets

Genus and species: *Solenostemon scutellariodes*.
Variety denomination: 'UF0843'.

BACKGROUND OF THE INVENTION

The invention relates to a new and distinct variety of coleus plant named 'UF0843'. 'UF0843' originated from an open pollination conducted in May-November 2008 in Gainesville, Fla. between the female coleus plant 'UF07106' (unpatented) and an unknown male coleus plant. A single seedling was chosen in May 2008 for further asexual propagation in Gainesville, Fla.

'UF0843' has been reproduced asexually for over three years through vegetative cuttings and has been found to retain its distinctive characteristics through successive asexual propagations.

Plant Breeder's Rights for this variety have been applied for in Canada on Apr. 6, 2011. 'UF0843' has not been made publicly available more than one year prior to the filing date of this application.

SUMMARY OF THE INVENTION

The following are the most outstanding and distinguishing characteristics of 'UF0843' when grown under normal horticultural practices in Gainesville, Fla.

1. Excellent color for both sunny and shady locations, with a uniform yellow-green foliage color under high light intensities;
2. Novel leaf shape;
3. Exceptional branching and growth habit;
4. Foliage retention for an extended period of time; and
5. Good sun and heat tolerance.

DESCRIPTION OF THE PHOTOGRAPHS

This new coleus plant is illustrated by the accompanying photographs which show the plant's form and foliage. The colors shown are as true as can be reasonably obtained by conventional photographic procedures. The photographs were taken from 3-month-old plants grown from cuttings in 5 inch pots and transplanted to display/trial gardens during June-August 2011 in Citra, Fla. and Gainesville, Fla.

DESCRIPTION OF THE NEW VARIETY

Figure 1:
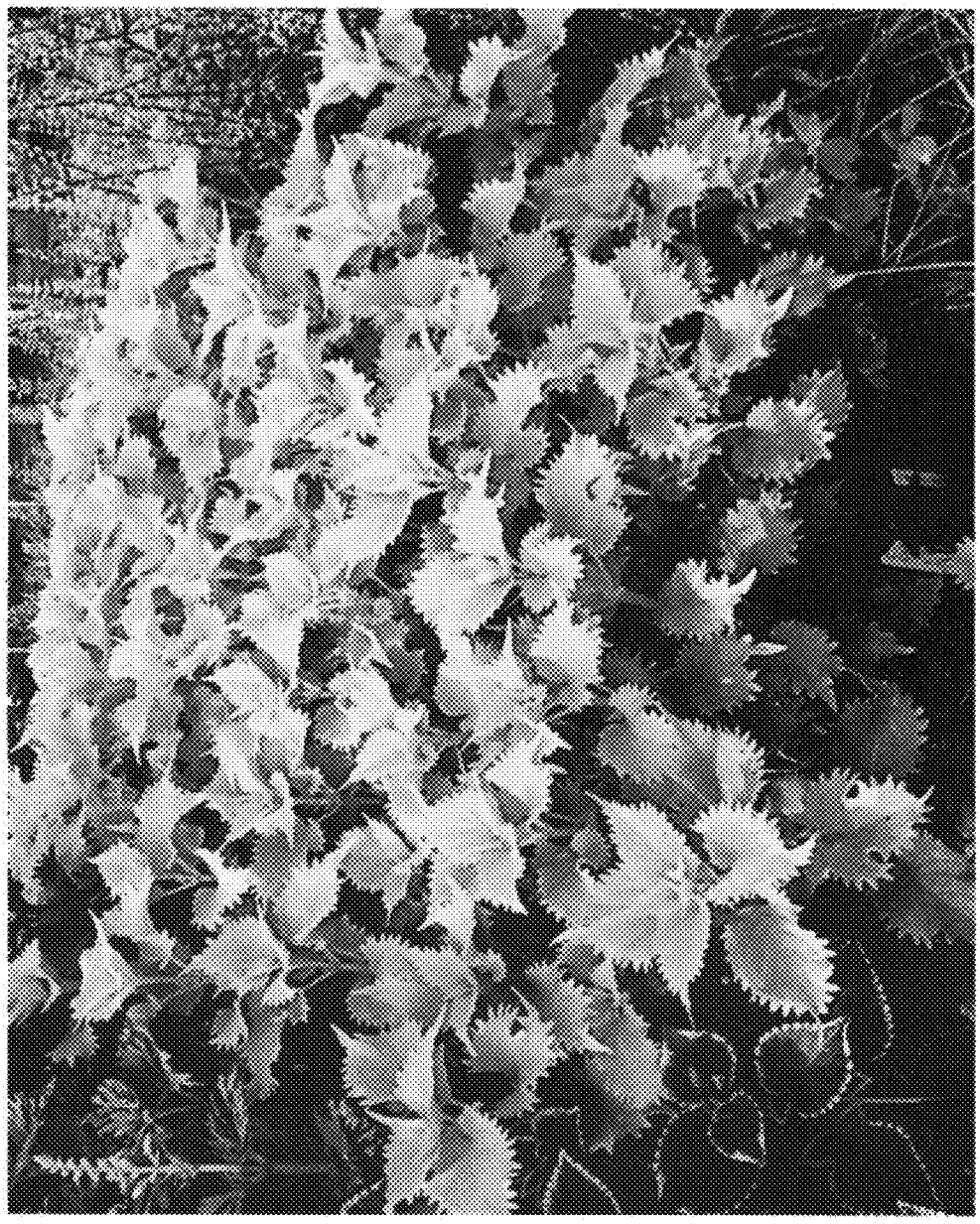
FIG. 1 shows the growth habit, form, and foliage of the instant plant.
Figure 2:
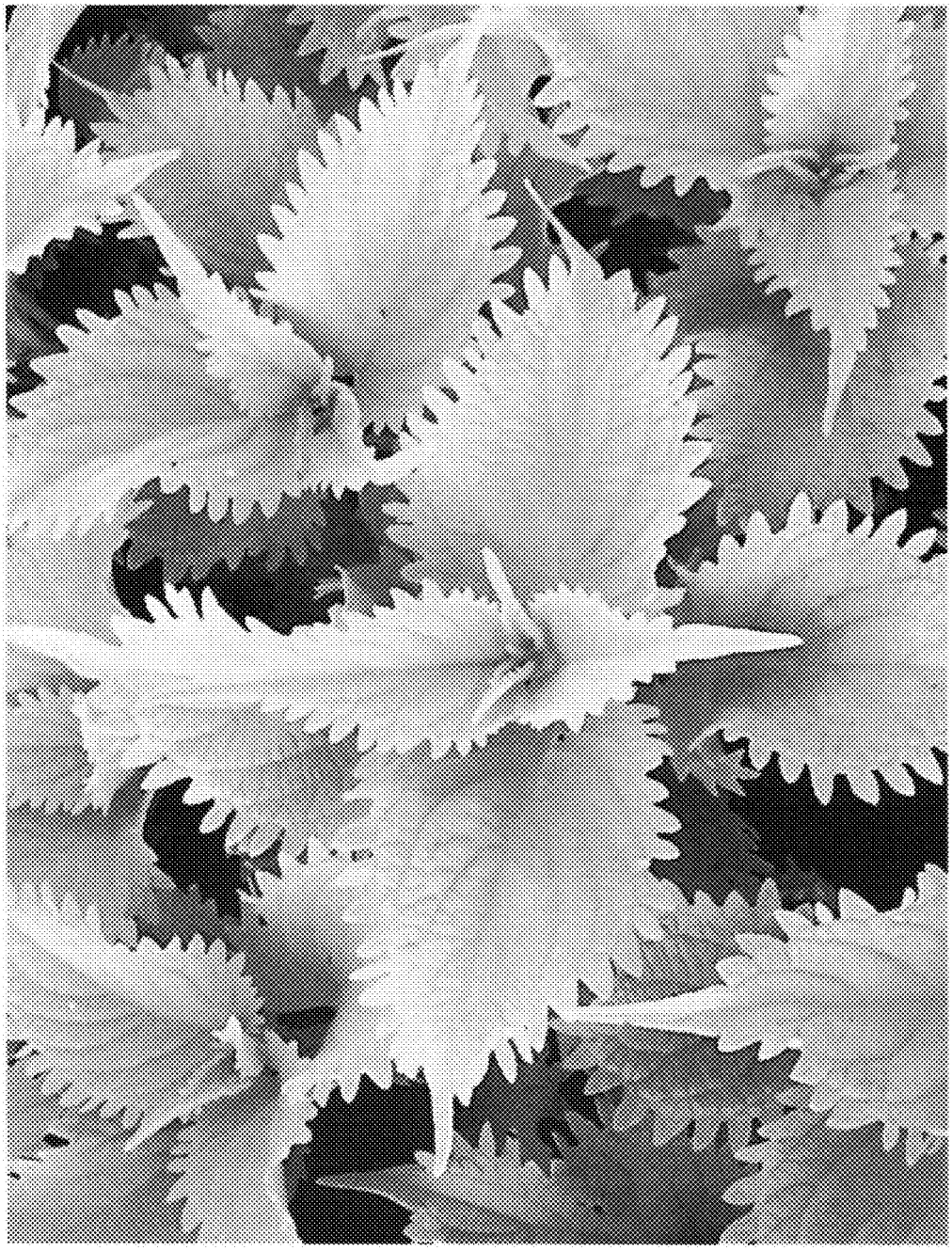
FIG. 2 shows a close-up of the foliage.

The following detailed description sets forth the distinctive characteristics of 'UF0843'. The detailed description was taken on 2-month-old plants from cuttings, growing in a glass greenhouse in Gainesville, Fla. in early spring 2011. The plants were pinched 2 weeks after cuttings were rooted, then grown in 1 gallon pots for approximately 10 weeks. Color references are to The R.H.S. Colour Chart of The Royal Horticultural Society of London (R.H.S.), 2001 Edition.

DETAILED BOTANICAL DESCRIPTION

Classification:
- *Family*.—Lamiaceae.
- *Botanical*.—*Solenostemon scutellariodes*.
- *Common name*.—Coleus.
- *Variety name*.—'UF0843'.

Plant description:
- *Form*.—Spreading.
- *Habit*.—Upright.
- *Height* (*from top of soil*).—50 cm.
- *Width* (*horizontal plant diameter*).—60 cm.

Propagation:
- *Type cuttings*.—Vegetative meristems having at least 1 node.
- *Time to initiate roots*.—3-4 days.
- *Time to produce a rooted cutting*.—7-10 days.
- *Root habit*.—Fibrous.
- *Root description*.—Callus forms in 2 to 3 days, roots initiate in 3-4 days and become a highly branched cutting in 7-10 days.

Branches:

*Quantity per plant.*—20 to 30 per plant, pinched once.

*Branch color.*—RHS 144A (yellow-green); nodes are banded RHS 59A (red-purple).

*Texture.*—Velvety.

*Pubescence.*—Non-descript.

*Stem description.*—Square shaped stem, 1.5 cm in diameter at the soil line.

*Branch diameter.*—0.6 cm at the base of a 16 cm long branch.

*Branch length.*—16 cm.

*Internode length.*—1.5-5 cm.

*Anthocyanin.*—N/A.

Leaves:

*Quantity of leaves per branch.*—10 to 15.

*Arrangement.*—Opposite.

*Fragrance.*—Not fragrant.

*Shape.*—Lacerate, consistent.

*Length.*—13-14 cm.

*Width.*—9-10 cm.

*Apex.*—Caudate.

*Base.*—Reticulate.

*Margin.*—Lacerate.

*Leaf texture (both surfaces).*—Slightly pubescent; velvet-like upper surface.

*Pubescence color (both surfaces).*—Non-descript with naked eye.

*Venation color.*—Upper surface: RHS 145C (yellow-green). Lower surface: RHS 145B (yellow-green).

*Venation pattern.*—Not distinct.

*Color, mature and immature leaf.*—Upper surface: RHS 151B (yellow-green) in the center of the leaf, transitioning to RHS 145B (yellow-green) margins. Lower surface: RHS 151C (yellow-green) transitioning to RHS 145B (yellow-green).

*Petiole length.*—1 cm to 4 cm.

*Petiole diameter.*—0.5 cm.

*Petiole color.*—RHS 145C (yellow-green).

Flowers, fruit, and seeds: Flowers, fruit, and seeds have not been observed.

Disease and insect resistance: Disease and insect resistance is typical of the species.

COMPARISON WITH PARENTAL LINES AND KNOWN VARIETY

When 'UF0843' is compared to the female parent 'UF07106' (unpatented), 'UF0843' has pure green foliage with bright green consistently lacerate-shaped leaves, while 'UF07106' had leaves colored maroon with green serrated leaf margins.

When 'UF0843' is compared to the commercial variety 'Hurricane Louise' (unpatented), plants of 'Hurricane Louise' have green-colored foliage with a pink-colored center that is irregularly and loosely lacerated around the leaf edge; whereas 'UF0843' has uniformly lacerated chartreuse foliage color and produces flowers later than 'Hurricane Louise'. When 'UF0843' is compared to the commercial variety 'UF04335' (unpatented) (marketed under ELECTRIC LIME® brand), plants of 'UF04335' have a distinctly darker green foliage color with distinct and wide chartreuse venation; whereas 'UF0843' has solid green-yellow/chartreuse foliage color. Leaf shape of 'UF04335' is attenuate at the base and acuminate at the tip with crenate margins as well.

We claim:

1. A new and distinct variety of coleus plant as shown and described herein.

* * * * *